United States Patent
Carroll et al.

(10) Patent No.: US 10,492,671 B2
(45) Date of Patent: Dec. 3, 2019

(54) NEAR INFRA RED FLUORESCENCE IMAGING FOR VISUALIZATION OF BLOOD VESSELS DURING ENDOSCOPIC HARVEST

(75) Inventors: Douglas R. Carroll, Concord, NC (US); Robert W. Flower, Hunt Valley, MD (US); John C. Docherty, Winnipeg (CA)

(73) Assignee: Novadaq Technologies ULC, Burnaby (CA)

( * ) Notice: Subject to any disclaimer, the term of this patent is extended or adjusted under 35 U.S.C. 154(b) by 1189 days.

(21) Appl. No.: 12/776,835

(22) Filed: May 10, 2010

(65) Prior Publication Data
US 2010/0286529 A1 Nov. 11, 2010

Related U.S. Application Data

(60) Provisional application No. 61/176,642, filed on May 8, 2009.

(51) Int. Cl.
| | | |
|---|---|---|
| *A61B 6/00* | (2006.01) |
| *A61K 41/00* | (2006.01) |
| *A61B 1/05* | (2006.01) |
| *A61B 1/00* | (2006.01) |

(Continued)

(52) U.S. Cl.
CPC .............. *A61B 1/05* (2013.01); *A61B 1/0005* (2013.01); *A61B 1/043* (2013.01); *A61B 5/0071* (2013.01); *A61B 5/0086* (2013.01); *A61B 5/489* (2013.01)

(58) Field of Classification Search
None
See application file for complete search history.

(56) References Cited

U.S. PATENT DOCUMENTS

| | | |
|---|---|---|
| 4,109,647 A | 8/1978 | Stern et al. |
| 4,162,405 A | 7/1979 | Chance et al. |
| 4,200,801 A | 4/1980 | Schuresko |
(Continued)

FOREIGN PATENT DOCUMENTS

| | | |
|---|---|---|
| AT | 409451 B | 8/2002 |
| CA | 2212257 A1 | 8/1996 |
(Continued)

OTHER PUBLICATIONS

"Taggart et al.," "Preliminary experiences with a novel intraoperative fluorescence imaging technique to evaluate the patency of bypass grafts in total arterial revascularization" Ann Thorac Surg 75:870-873, 2003.*

(Continued)

*Primary Examiner* — Patricia J Park
(74) *Attorney, Agent, or Firm* — Morrison & Foerster LLP

(57) ABSTRACT

Endoscopic identification and dissection of a blood vessel in tissue during endoscopic harvest can be enhanced by injecting a bolus of ICG into the bloodstream, illuminating the target vessels with excitation light capable of exciting fluorescence in the ICG, and locating the vessel to be harvested by observing the ICG fluorescence. Moreover, collapsed blood vessel may be harvested by inserting an endoscope into the collapsed blood vessel, injecting into the collapsed blood vessel a bolus containing ICG to re-inflate the blood vessel, illuminating the target vessels with excitation light capable of exciting fluorescence in the ICG; and locating the re-inflated blood vessel by observing the ICG fluorescence.

20 Claims, 2 Drawing Sheets

(51) Int. Cl.
*A61B 1/04* (2006.01)
*A61B 5/00* (2006.01)

(56) References Cited

U.S. PATENT DOCUMENTS

| | | |
|---|---|---|
| 4,263,916 A | 4/1981 | Brooks et al. |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 6/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,491,343 A | 2/1996 | Brooker |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,603,552 B1 | 8/2003 | Cline et al. |

(56) References Cited

U.S. PATENT DOCUMENTS

| | | |
|---|---|---|
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 * | 9/2005 | Alam et al. .................. 600/431 |
| 7,113,817 B1 | 9/2006 | Winchester, Jr. et al. |
| 7,236,815 B2 | 6/2007 | Richards-Kortum et al. |
| 7,364,574 B2 | 4/2008 | Flower |
| 7,381,400 B2 | 6/2008 | Woltering |
| 7,400,753 B2 | 7/2008 | Seino et al. |
| 7,400,755 B2 | 7/2008 | West et al. |
| 7,482,318 B2 | 1/2009 | Aurelian et al. |
| 7,581,191 B2 | 8/2009 | Rice et al. |
| 7,729,750 B2 | 6/2010 | Tromberg et al. |
| 7,774,048 B2 | 8/2010 | Nakaoka et al. |
| 7,881,777 B2 | 2/2011 | Docherty et al. |
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,194,981 B2 | 6/2012 | Suzuki |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Röttger |
| 8,647,605 B2 | 2/2014 | Mangat et al. |
| 8,725,225 B2 | 5/2014 | Golijanin et al. |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,089,601 B2 | 7/2015 | Golijanin et al. |
| 9,129,366 B2 | 9/2015 | Nahm et al. |
| 9,241,636 B2 | 1/2016 | Koizumi et al. |
| RE45,916 E | 3/2016 | Golijanin et al. |
| 9,351,644 B2 | 5/2016 | Nahm et al. |
| 9,357,931 B2 | 6/2016 | Nahm et al. |
| 9,421,280 B2 | 8/2016 | Mangat et al. |
| 9,610,021 B2 | 4/2017 | Dvorsky et al. |
| 9,642,532 B2 | 5/2017 | Fengler et al. |
| 9,816,930 B2 | 11/2017 | Moriyama et al. |
| 9,936,887 B2 | 4/2018 | Dvorsky et al. |
| 10,041,042 B2 | 8/2018 | Flower |
| 2002/0025541 A1 | 2/2002 | Nelson et al. |
| 2002/0038120 A1 * | 3/2002 | Duhaylongsod et al. ...... 606/15 |
| 2002/0099279 A1 | 7/2002 | Pfeiffer et al. |
| 2002/0099295 A1 | 7/2002 | Gil et al. |
| 2002/0146369 A1 | 10/2002 | Goldenberg |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0156252 A1 | 8/2003 | Morris et al. |
| 2003/0187349 A1 * | 10/2003 | Kaneko et al. ............... 600/425 |
| 2003/0232016 A1 | 12/2003 | Heinrich |
| 2003/0236458 A1 | 12/2003 | Hochman |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0069525 A1 | 3/2005 | Mikael |
| 2005/0089866 A1 | 4/2005 | Hinuma et al. |
| 2005/0107380 A1 | 5/2005 | Nimmo et al. |
| 2005/0142556 A1 | 6/2005 | Hoon et al. |
| 2005/0182321 A1 | 8/2005 | Frangioni |
| 2005/0182327 A1 | 8/2005 | Petty et al. |
| 2005/0182431 A1 * | 8/2005 | Hausen et al. ................ 606/153 |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0118742 A1 | 6/2006 | Levenson et al. |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0121099 A1 | 5/2007 | Matsumoto et al. |
| 2007/0122344 A1 | 5/2007 | Golijanin |
| 2007/0122345 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0025918 A1 | 1/2008 | Frangioni et al. |
| 2008/0044073 A1 | 2/2008 | Bernhardt et al. |
| 2008/0081990 A1 | 4/2008 | Berenfeld et al. |
| 2008/0161744 A1 | 7/2008 | Golijanin et al. |
| 2008/0221421 A1 | 9/2008 | Choi et al. |
| 2008/0221648 A1 | 9/2008 | Flower |
| 2008/0239070 A1 * | 10/2008 | Westwick et al. ............... 348/68 |
| 2008/0319309 A1 | 12/2008 | Bredno et al. |
| 2009/0005693 A1 | 1/2009 | Brauner et al. |
| 2009/0042179 A1 | 2/2009 | Peltie et al. |
| 2009/0048516 A1 | 2/2009 | Yoshikawa et al. |
| 2009/0054788 A1 | 2/2009 | Hauger et al. |
| 2009/0118623 A1 | 5/2009 | Serov et al. |
| 2009/0137902 A1 | 5/2009 | Frangioni et al. |
| 2009/0252682 A1 | 10/2009 | Hillman |
| 2009/0297004 A1 | 12/2009 | Baumgart |
| 2010/0022898 A1 | 1/2010 | Rubinstein et al. |
| 2010/0036217 A1 | 2/2010 | Choi et al. |
| 2010/0061604 A1 | 3/2010 | Nahm et al. |
| 2010/0222673 A1 | 9/2010 | Mangat et al. |
| 2011/0001061 A1 | 1/2011 | Ishihara |
| 2011/0013002 A1 | 1/2011 | Thompson et al. |
| 2011/0063427 A1 | 3/2011 | Fengler et al. |
| 2011/0071403 A1 | 3/2011 | Sevick-Muraca et al. |
| 2011/0098685 A1 | 4/2011 | Flower |
| 2011/0306877 A1 | 12/2011 | Dvorsky et al. |
| 2012/0026325 A1 | 2/2012 | Bunker et al. |
| 2012/0078093 A1 | 3/2012 | Flower |
| 2012/0165662 A1 | 6/2012 | Nahm et al. |
| 2012/0271176 A1 | 10/2012 | Moghaddam et al. |
| 2013/0230866 A1 | 9/2013 | Miyashita et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0345560 A1 | 12/2013 | Ferguson, Jr. et al. |
| 2014/0099007 A1 | 4/2014 | Sarkar et al. |
| 2014/0308656 A1 | 10/2014 | Flower |
| 2014/0316262 A1 | 10/2014 | Havens |
| 2015/0112192 A1 | 4/2015 | Docherty et al. |
| 2015/0112193 A1 | 4/2015 | Docherty et al. |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2016/0038027 A1 | 2/2016 | Brzozowski et al. |
| 2016/0041098 A1 | 2/2016 | Hirawake et al. |
| 2016/0199515 A1 | 7/2016 | Flower |
| 2016/0371834 A1 | 12/2016 | Watanabe et al. |
| 2017/0039710 A1 | 2/2017 | Minai et al. |

(56) References Cited

U.S. PATENT DOCUMENTS

| | | | |
|---|---|---|---|
| 2017/0303800 | A1 | 10/2017 | Flower et al. |
| 2018/0020933 | A1 | 1/2018 | Dvorsky et al. |
| 2018/0104362 | A1 | 4/2018 | Golijanin et al. |
| 2018/0120230 | A1 | 5/2018 | Moriyama et al. |
| 2018/0220907 | A1 | 8/2018 | Dvorsky et al. |
| 2018/0234603 | A1 | 8/2018 | Moore et al. |

FOREIGN PATENT DOCUMENTS

| | | |
|---|---|---|
| CA | 2413033 A1 | 3/2000 |
| CA | 2711560 A1 | 7/2009 |
| CN | 1049781 A | 3/1991 |
| CN | 1200174 A | 11/1998 |
| CN | 1399528 A | 2/2003 |
| CN | 101264014 A | 9/2008 |
| DE | 3906860 A1 | 9/1989 |
| DE | 19608027 A1 | 9/1996 |
| DE | 10028233 A1 | 1/2002 |
| DE | 10120980 A1 | 11/2002 |
| DE | 69727220 T2 | 12/2004 |
| DE | 102005044531 A1 | 3/2007 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0807402 A1 | 11/1997 |
| EP | 0826335 A1 | 3/1998 |
| EP | 1677097 A1 | 7/2006 |
| EP | 1761171 | 3/2007 |
| EP | 1874181 | 1/2008 |
| GB | 2203831 A | 10/1988 |
| JP | S58-222331 A | 12/1983 |
| JP | S59-069721 A | 4/1984 |
| JP | S59-070903 A | 4/1984 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | H07-043303 A | 2/1995 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-500479 A | 1/1998 |
| JP | H10-503480 A | 3/1998 |
| JP | H10-085222 A | 4/1998 |
| JP | H10-104070 A | 4/1998 |
| JP | H10-151104 A | 6/1998 |
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2001-198079 A | 7/2001 |
| JP | 2002-219129 A | 8/2002 |
| JP | 2003-510121 A | 3/2003 |
| JP | 2003-144401 A | 5/2003 |
| JP | 2003-329589 A | 11/2003 |
| JP | 2004-528917 A | 9/2004 |
| JP | 2004-325200 A | 11/2004 |
| JP | 2006-503620 A | 2/2006 |
| JP | 2006-192280 A | 7/2006 |
| JP | 2007-021006 A | 2/2007 |
| JP | 3896176 B2 | 3/2007 |
| JP | 2008-525126 A | 7/2008 |
| JP | 2008-535600 A | 9/2008 |
| JP | 2008-231113 A | 10/2008 |
| JP | 2009-095683 A | 5/2009 |
| JP | 2009-291554 A | 12/2009 |
| JP | 2010-505582 A | 2/2010 |
| JP | 2011-509768 A | 3/2011 |
| JP | 2011-519589 A | 7/2011 |
| JP | 2011-528918 A | 12/2011 |
| JP | 5918532 B2 | 5/2016 |
| KR | 90-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO-1993/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/061390 A2 | 8/2002 |
| WO | WO-2003/006658 A1 | 1/2003 |
| WO | WO-2004/006963 A1 | 1/2004 |
| WO | WO-2004/052195 A1 | 6/2004 |
| WO | WO-2005/026319 A2 | 3/2005 |
| WO | WO-2005/034747 A1 | 4/2005 |
| WO | WO-2005/036143 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2008/039968 A2 | 4/2008 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |

(56) References Cited

FOREIGN PATENT DOCUMENTS

| WO | WO-2013/190391 A2 | 12/2013 |
|---|---|---|
| WO | WO-2015/001427 A2 | 1/2015 |
| WO | WO-2013/002350 A1 | 2/2015 |

OTHER PUBLICATIONS

"Flower," "Injection technique for indocyanine green and sodium fluorescein dye angiography of the eye," Investigative Opthamology, vol. 2 No. 12, pp. 881-895, 1973.*
"Kuipers et al.," "Recirculatory and Compartmental Pharmacokinetic Modeling of Alfentanil Pigs," Anesthesiology, 90:1146-57, 1999.*
Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience Methods* 45(1-2):15-22.
Alander, J.T. et al. (Jan. 1, 2012). "A Review of Indocyanine Green Fluorescent Imaging in Surgery," *International Journal of Biomedical Imaging* 2012:1-26, article ID 940585.
Alfano et al. (Oct. 1987). "Fluorescence Spectra from Cancerous and Normal Human Breast and Lung Tissues," *IEEE Journal of Quantum Electronics* QE-23(10):1806-1811.
Alm, A. et al. (Jan. 1, 1973). "Ocular and Optic Nerve Blood Flow at Normal and Increased Intraocular Pressures in Monkeys (Macaca irus): A Study with Radioactively Labelled Microspheres Including Flow Determinations in Brain and Some Other Tissues," *Experimental Eye Research* 15(1):15-29.
Alonso-Burgos, A. et al.(2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.
Alvarez, F. J. et al. (Apr. 1996). "Behaviour of Isolated Rat and Human Red Blood Cells Upon Hypotonic-Dialysis Encapsulation of Carbonic Anhydrase and Dextran," *Biotechnology and Applied Biochemistry* 23(2):173-179.
Ancalmo, N. et al. (1997). "Minimally invasive coronary artery bypass surgery: really minimal?" *Ann. Thorac. Surg.* 64:928-929.
Andersson-Engels, S. et al. (1991). "Fluorescence Characteristics of Atherosclorotic Plaque and Malignant Tumors," in *Optical Methods for Tumor Treatment and Early Diagnosis: Mechanisms and Techniques*, T. J. Dougherty (Ed.), The Society of Photo-optical Instrumentation Engineers (SPIE) 1426:31-43, fourteen pages.
Andersson-Engels, S. et al. (Mar. 1989). "Tissue Diagnostics Using Laser-Induced Fluorescence," *Berichte der Bunsengesellschaft für physikalische Chemie* 93(3):335-342.
Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.
Annese, V. et al. (2005). "Erthrocytes-Mediated Delivery of Dexamethasone in Steroid-Dependent IBD Patients—a Pilot Uncontrolled Study," *American Journal of Gastroenterology* 100:1370-1375.
Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.
Author Unknown. (Jun. 4, 2008)."Invitrogen," Material Safety Data Sheet, p. 1-4.
Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.
Azuma, R. et al. (2008, presented in part Jun. 2007). "Detection of Skin Perforators by Indocyanine Green Fluorescence Nearly Infrared Angiography," *PRS Journal* 122(4):1062-1067.

Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.
Barton, J.K. et al. (1999) "Simultaneous irradiation and imaging of blood vessels during pulsed laser delivery," *Lasers in Surgery and Medicine* 24(3):236-243.
Bassingthwaighte, J.B. et al. (Apr. 1974). "Organ Blood Flow, Wash-in, Washout, and Clearance of Nutrients and Metabolites," *Mayo Clin. Proc.* 49(4):248-255.
Batliwala, H. et al. (Apr. 15, 1995). "Methane-Induced Haemolysis of Human Erythrocytes," *Biochemical J.* 307(2):433-438.
Bek, T. (1999). "Diabetic Maculopathy Caused by Disturbances in Retinal Vasomotion: A New Hypothesis," *Acta Ophthalmologica Scandinavica* 77:376-380.
Benson, R.C. et al. (1978). "Fluorescence Properties of Indocyanine Green as Related to Angiography," *Phys. Med. Biol.* 23(1):159-163.
Black's Medical Dictionary, "Perfusion," 42nd Edition (2009), two pages.
Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.
Boldt, .J. et al. (Feb. 1990). "Lung management during cardiopulmonary bypass: influence on extravascular lung water," *Journal of Cardiothoracic Anesthesia* 4(1):73-79.
Boldt, J. et al. (1991). "Does the technique of cardiopulmonary bypass affect lung water content?" *European Journal of Cardio-Thoracic Surgery* 5:22-26.
Bütter, A. et al. (May 2005). "Melanoma in Children and the Use of Sentinel Lymph Node Biopsy," *Journal of Pediatric Surgery* 40(5):797-800.
C2741, Compact High Performance video camera for industrial applications with Built-in contrast enhancement circuit, Jun. 1998, six pgs.
Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.
Coffey, J.H. et al. (1984). "Evaluation of Visual Acuity During Laser Photoradiation Therapy of Cancer," *Lasers in Surgery and Medicine* 4(1):65-71.
Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.
Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.
Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.
Dail, W.G. et al. (Oct. 1999). "Multiple Vasodilator Pathways from the Pelvic Plexus to the Penis of the Rat," *International Journal of Impotence Research* 11(5):277-285.
Dan, A.G. et al. (Nov. 2004). "1% Lymphazurin vs 10% Fluorescein for Sentinel Node Mapping in Colorectal Tumors," *Arch Surg.* 139(11):1180-1184.
Daniels, G. et al. (Apr. 2007). "Towards Universal Red Blood Cell," *Nature Biotechnology* 25(4):427-428.
De Flora, A. (Sep. 1986). "Encapsulation of Adriamycin in human erythrocytes," *Proc. Natl. Acad. Sci., USA* 83(18):7029-7033.
Declaration of Brian Wilson dated Aug. 22, 2017 for Inter Partes Review No. IPR2017-01426, twelve pages.
Definition of "Expose," Excerpt of Merriam Webster's Medical Desk Dictionary (1993), four pages.
Definition of "Graft," Excerpt of Stedman's Medical Dictionary for the Health Professions and Nursing; 6th Ed. (2008), three pages.
De-Grand, A.M. et al. (Dec. 2003). "An Operational Near Infrared Fluorescence Imaging System Prototype for Large Animal Surgery," *Technology in Cancer Research & Treatment* 2(6):1-10.
Deloach, J.R. (ed.) et al. (1985). Red Blood Cells as Carriers for Drugs. A Method for Disseminating Chemotherapeutics, Hormones, Enzymes and Other Therapeutic Agents via the Circulatory System, Karger, Basel, CH, pp. v-vii, (Table of Contents), seven pages.

(56) References Cited

OTHER PUBLICATIONS

Deloach, J.R. (Jun. 1983). "Encapsulation of Exogenous Agents in Erythrocytes and the Circulating Survival of Carrier Erythrocytes," *Journal of Applied Biochemistry* 5(3):149-157.

Demos (May/Jun. 2004). "Near-Infrared Autofluorescence Imaging for Detection of Cancer," *Journal of Biomedical Optics* 9(3):587-592.

Desai, N.D. et al. (Oct. 18, 2005, e-published on Sep. 28, 2005) "Improving the Quality of Coronary Bypass Surgery with Intraoperative Angiography," *Journal of the American College of Cardiology* 46(8):1521-1525.

Detter, C. et al. (Aug. 28, 2007). "Fluorescent Cardiac Imaging: A Novel Intraoperative Method for Quantitative Assessment of Myocardial Perfusion During Graded Coronary Artery Stenosis," *Circulation* 116(9):1007-1014.

Detter, C. et al. (Jun. 2002). "Near-Infrared Fluorescence Coronary Angiography: A New Noninvasive Technology for Intraoperative Graft Patency Control." *The Heart Surgery Forum* #2001-6973 5(4):364-369.

Dietz, F.B. et al. (Feb. 2003). "Indocyanine Green: Evidence of Neurotoxicity in Spinal Root Axons," *Anesthesiology* 98(2):516-520.

Digital CCD Microscopy (date unknown). Chapter 14, pp. 259-282.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed CMOS-Camera," in *Novel Optical Instrumentation for Biomedical Applications III*, C. Depeursinge, ed., Proceedings of SPIE-OSA Biomedical Optics (Optical Society of America, 2007), SPIE-OSA, 6631:0N1-0N7, eight pages.

Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

Enquist, L.W. et al. (2002). "Directional Spread of an α-Herpesvirus in the Nervous System," *Veterinary Microbiology* 86:5-16.

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.

Flower, R.W. (1992)."Choroidal Angiography Today and Tomorrow," *Retina* 12(3):189-190.

Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.

Flower, R.W. (Aug. 2002). "Optimizing Treatment of Choroidal Neovascularization Feeder Vessels Associated with Age-Related Macular Degeneration," *American Journal of Ophthalmology* 134(2):228-239.

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," *Investigative Ophthalmology, & Visual Science* 49(12):5510-5516.

Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).

Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.

Frangioni, J.V. (Oct. 2003). "In Vivo Near-Infrared Fluorescence Imaging," *Current Opinion in Chemical Biology* 7(5):626-634.

Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.

Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.

Gagnon, A.R. et al. (2006). "Deep and Superficial Inferior Epigastric Artery Perforator Flaps," *Cirugia Plástica Ibero-Latinoamericana* 32(4):7-13.

Gardner, T.J. (1993). "Coronary Artery Disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.

Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.

Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal Of Physical Chemistry A* 107(18):3443-3449.

Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.

Giunta, R.E. et al. (Jul. 2005). "Prediction of Flap Necrosis with Laser Induced Indocyanine Green Fluorescence in a Rat Model," *British Journal of Plastic Surgery* 58(5):695-701.

Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nl0/glossary/nrgl 183_glossary.html» HTML on Jun. 30, 2014, three pages.

Glover, J.C. et al. (Nov. 1986). "Fluorescent Dextran-Amines Used as Axonal Tracers in the Nervous System of the Chicken Embryo," *Journal of Neuroscience Methods* 18(3):243-254.

Goldstein, J.A. et al. (Dec. 1998). "Intraoperative Angiography to Assess Graft Patency After Minimally Invasive Coronary Bypass," *Ann. Thorac. Surg.* 66(6):1978-1982.

Gothoskar A.V. (Mar. 2004). "Resealed Erythrocytes: A Review," *Pharmaceutical Technology* pp. 140, 142, 144, 146, 148, 150, 152 and 154-158, twelve pages.

Granzow, J.W. et al. (Jul. 2007)."Breast Reconstruction with Perforator Flaps" *Plastic and Reconstructive Surgery* 120(1):1-12.

Green, H.A. et al. (Jan. 1992). "Burn Depth Estimation Using Indocyanine Green Fluorescence," *Arch Dermatol* 128(1):43-49.

Haglund, M. et al. (Feb. 1996). "Enhanced Optical Imaging of Human Gliomas and Tumor Margins," *Neurosurgery* 38(2):308-317.

Haglund, M.M. et al. (Nov. 1994). "Enhanced Optical Imaging of Rat Gliomas and Tumor Margins," *Neurosurgery* 35(5):930-941.

Hallock, G.G. (Jul. 2003). "Doppler Sonography and Color Duplex Imaging for Planning a Perforator Flap," *Clinics in Plastic Surgery* 30(3):347-357.

(56) References Cited

OTHER PUBLICATIONS

Hamamatsu Brochure. (May 1997). Specifications for Real-time Microscope Image Processing System: ARGUS-20 with C2400-75i, four pages.

Hamamatsu. (Date unknown). Microscope Video Camera, For Fluorescent Observation, Easy Fluorescent Image Analysis C2400-73I, -75I Series a CCD Camera, seven pages.

Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.

Hayata, Y. et al. (Jul. 1982). "Fiberoptic Bronchoscopic Laser Photoradiation for Tumor Localization in Lung Cancer," *Chest* 82(1):10-14.

He, Z. (Feb. 2009). "Fluorogold Induces Persistent Neurological Deficits and Circling Behavior in Mice Over-Expressing Human Mutant Tau," *Current Neurovascular Research* 6(1):54-61.

Herts, B.R. (May 2003). "Imaging for Renal Tumors," *Current Opin.. Urol.* 13(3):181-186.

Hirano, T. et al. (1989). "Photodynamic Cancer Diagnosis and Treatment System Consisting of Pulse Lasers and an Endoscopic Spectro-Image Analyzer," *Laser in Life Sciences* 3(2):99-116.

Holm, C. et al. (2002). "Monitoring Free Flaps Using Laser-Induced Fluorescence of Indocyanine Green: A Preliminary Experience," *Microsurgery* 22(7):278-287.

Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.

Holm, C. et al. (Dec. 1, 2002). "Intraoperative Evaluation of Skin-Flap Viability Using Laser-Induced Fluorescence of Indocyanine Green," *British Journal of Plastic Surgery* 55(8):635-644.

Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.

Hung, J. et al. (1991). "Autofluorescence of Normal and Malignant Bronchial Tissue," *Lasers in Surgery and Medicine* 11(2):99-105.

Hyvärinen, L. et al. (1980). "Indocyanine Green Fluorescence Angiography." *Acta ophthalmologica* 58(4):528-538.

Ikeda, S. (Jul. 1989). "Bronichial Telivision Endoscopy," *Chest* 96(1):41S-42S.

Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.

Jagoe, J.R. et al. (1989). "Quantification of retinal damage during cardiopulmonary bypass," Third International Conference on Image Processing and its Applications (Conf. Publ. No. 307), IEE, pp. 319-323.

Jamis-Dow, C.A. et al. (Mar. 1996). "Small (< or = 3-cm) Renal Masses: Detection with CT versus US and Pathologic Correlation," *Radiology* 198(3):785-788.

Jolion, J. et al. (Aug. 1991). "Robust Clustering with Applications in Computer Vision," *IEEE Transactions on Pattern Analysis and Machine Intelligence* 13(8):791-802.

Kamolz, L.-P. et al. (Dec. 2003). "Indocyanine Green Video Angiographies Help to Identify Burns Requiring Operation," *Burns* 29(8):785-791.

Kapadia, C.R. et al. (Jul. 1990). "Laser-Induced Fluorescence Spectroscopy of Human Colonic Mucosa. Detection of Adenomatous Transformation," *Gastroenterology* 99(1):150-157.

Kato, H. et al. (Jun. 1985). "Early Detection of Lung Cancer by Means of Hematoporphyrin Derivative Fluorescence and Laser Photoradiation," *Clinics in Chest Medicine* 6(2):237-253.

Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.

Keon, W.J. et al. (Dec. 1979). "Coronary Endarterectomy: An Adjunct to Coronary Artery Bypass Grafting," *Surgery* 86(6):859-867.

Kim, S. et al. (Jan. 2004, e-published Dec. 7, 2003). "Near-Infrared Fluorescent Type II Quantum Dots for Sentinel Lymph Node Mapping," *Nature Biotechnology* 22(1):93-97.

Kiryu, J. et al. (Sep. 1994). "Noninvasive Visualization of the Choriocapillaris and its Dynamic Filling," *Investigative Ophthalmology & Visual Science* 35(10):3724-3731.

Kitai, T. et al. (Jul. 2005). "Fluorescence Navigation with Indocyanine Green for Detecting Sentinel Lymph Nodes in Breast Cancer," *Breast Cancer* 12(3):211-215.

Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.

Köbbert, C. et al. (Nov. 2000). "Current Concepts in Neuroanatomical Tracing," *Progress in Neurobiology* 62(4):327-351.

Kokaji, K. et al. (Date Unknown). "Intraoperative Quality Assessment by Using Fluorescent Imaging in Off-pump Coronary Artery Bypass Grafting," *The Department of Cardiovascular Surgery, University of Keio*, Tokyo, Japan, one page. (Abstract only).

Kömürcü, F. et al. (Feb. 2005). "Management Strategies for Peripheral Iatrogenic Nerve Lesions," *Annals of Plastic Surgery* 54(2):135-139.

Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.

Kupriyanov, V.V. et al. (Nov. 2004; , e-publication Sep. 28, 2004). "Mapping Regional Oxygenation and Flow in Pig Hearts In Vivo Using Near-infrared Spectroscopic Imaging," *Journal of Molecular and Cellular Cardiology* 37(5):947-957.

Kurihara, K. et al. (Jun. 1984). "Nerve Staining with Leucomethylene Blue: an Experimental Study," *Plastic and Reconstruction Surgery* 73(6):960-964.

Kyo, S. (Date Unknown). "Use of Ultrasound Cardiology during Coronary Artery Bypass Surgery," *Heart and Blood Vessel Imaging II*, three pages.

Lam, S. et al. (1991). "Mechanism of Detection of Early Lung Cancer by Ratio Fluorometry," *Lasers in Life Sciences* 4(2):67-73.

Lam, S. et al. (Feb. 1990). "Detection of Early Lung Cancer Using Low Dose Photofrin II," *Chest* 97(2):333-337.

Lam, S. et al. (Jul. 1, 1990). "Detection of Lung Cancer by Ratio Fluorometry With and Without Photofrin II," *Proc. SPIE—Optical Fibers in Medicine V* 1201:561-568.

Lam, S. et al. (Nov. 1-4, 1990). "Fluorescence Imaging of Early Lung Cancer," *Annual International Conference of the IEEE Engineering in Medicine and Biology Society* 12(3):1142-1143.

Lam, S.C. et al. (1993). "Fluorescence Detection," Chapter 20 in *Lung Cancer* Roth, J.A. (ed.), et al., Blackwell Scientific Publications Inc., 238 Main Street, Cambridge, Massachusetts, 02142, pp. 325-338, sixteen pages.

Lanciego, J.L. et al. (Jun. 1998). "Multiple Neuroanatomical Tracing in Primates," *Brain Research Protocols* 2(4):323-332.

Lanciego, J.L. et al. (Oct. 1998). "Multiple Axonal Tracing: Simultaneous Detection of Three Tracers in the Same Section," *Histochemistry and Cell Biology* 110(5):509-515.

Laub, G.W. et al. (Nov. /Dec. 1989). "Experimental Use of Fluorescein for Visualization of Coronary Arteries," *Vascular and Endovascular Surgery* 23(6):454-457.

Lee, E.T. et al. (Mar. 1997). "A New Method for Assessment of Changes in Retinal Blood Flow," *Medical Engineering & Physics* 19(2):125-130.

Leissner, J. et al. (Jan. 2004). "Extended Radical Lymphadenectomy in Patients with Urothelial Bladder Cancer: Results of a Prospective Multicenter Study," *The Journal of Urology* 171(1):139-144.

Leithner, C. (Jul. 14, 2003). "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/d issertationen/leith nerch ristoph-2003-07-14/>, two hundred and eight pages, (English Abstract and Machine Translation).

Liedberg, F. et al. (2003). "Sentinel-Node-Diagnostik Beim Invasiven (Bladder Cancer and the Sentinel Node Concept)," *Aktuel Urol.* 34:115-118, (English Abstract Only).

(56) References Cited

OTHER PUBLICATIONS

Liedberg, F. et al. (Jan. 2006). "Intraoperative Sentinel Node Detection Improves Nodal Staging in Invasive Bladder Cancer," *The Journal of Urology* 175(1):84-89.

Lippincott's New Medical Dictionary. "Perfusion," p. 707 (1897), three pages.

Liptay, M.J. (Mar. 2004). "Sentinel Node Mapping in Lung Cancer," *Annals of Surgical Oncology* 11(Supplement 3):271S-274S.

Little, J.R. et al. (May 1979). "Superficial Temporal Artery to Middle Cerebral Artery Anastomosis: Intraoperative Evaluation by Fluorescein Angiography and Xenon- 133 Clearance," *Journal of Neurosurgery* 50(5):560-569.

Liu Q. P. et al. (Apr. 2007). "Bacterial Glycosidases for the Production of Universal Red Blood Cells" *Nature Biotechnology* 25(7):454-464.

Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.

Mack, M.J. et al. (Sep. 1998). "Arterial Graft Patency in Coronary Artery Bypass Grafting: What Do We Really Know?," *Ann. Thorac. Surg.* 66(3):1055-1059.

Magnani, M. et al. (1998). "Erythrocyte Engineering for Drug Delivery and Targeting," *Biotechnol. Appl. Biochem.* 28:1-6.

Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.

Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.

Marangos, N. et al. (Dec. 2001). "In Vivo Visualization of the Cochlear Nerve and Nuclei with Fluorescent Axonal Tracers," *Hearing Research* 162(1-2):48-52.

Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.

May, S. (May/Jun. 1995). "Photonic Approaches to Burn Diagnostics," *Biophotonics International* pp. 44-50.

Mckee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.

Merriam Webster Medline Plus Medical Dictionary. "Perfusion," located at http://www.merriam-webster.com/medlineplus/perfusion, last visited on Apr. 15, 2015, one page.

Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.

Mitaka USA, Inc. (2015). "PDE Breast Free Flap Evaluation," located at <http://mitakausa.com/category/pde_education/flaps/>, last visited on Oct. 7, 2016, four pages.

Mitaka USA, Inc. (2015). "PDE-Neo" located at <http://mitakausa.com/pde-neo/>, last visited on Oct. 7, 2016, two pages.

Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.

Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.

Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-1024.

Motomura, K. et al. (1999). "Sentinel Node Biopsy Guided by Indocyanine Green Dye in Breast Cancer Patients," *Japan J. Clin. Oncol.* 29(12):604-607.

Mullooly, V.M. et al. (1990). "Dihematoporphyrin Ether-Induced Photosensitivity in Laryngeal Papilloma Patients," *Lasers in Surgery and Medicine* 10(4):349-356.

Murphy (2001). "Digital CCD Microscopy," Chapter 14 in *Fundamentals of Light Microscopy and Electronic Imaging*, John Wiley and Sons, pp. i-xi and 259-281.

Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.

Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366, seventeen pages.

Nakayama, A. et al. (Oct. 2002). "Functional Near-Infrared Fluorescence Imaging for Cardiac Surgery and Targeted Gene Therapy," *Molecular Imaging* 1(4):365-377.

Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.

Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.

Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.

Novadaq Technologies Inc. (Jan. 29, 2007). "Novadaq Imaging System Receives FDA Clearance for use During Plastic Reconstructive Surgery," *PR Newswire*, three pages.

Novadaq Technologies Inc. (Jan. 19, 2005). 510(k) Summary—Showing X-Ray Fluoroscopy as Predicate Device, Fluorescent Angiographic System, six pages.

Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.

Ogata, F. et al. (Jun. 2007). "Novel Lymphography Using Indocyanine Green Dye for Near-Infrared Fluorescence Labeling," *Annals of Plastic Surgery* 58(6):652-655.

Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.

Ooyama, M. (Oct. 12-15, 1994). The 8th Congress Of International YAG Laser Symposium, The 15th Annual Meeting of Japan Society for Laser Medicine, Sun Royal Hotel, Japan, eight pages.

Ott, P. (1998). "Hepatic Elimination of Indocyanine Green with Special Reference to Distribution Kinetics and the Influence of Plasma Protein Binding," *Pharmacology & Toxicology* 83(Supp. II):5-48.

Oxford Concise Medical Dictionary. "Perfusion," p. 571 (1980), three pages.

Pagni, S. et al. (Jun. 1997). "Anastomotic Complications in Minimally Invasive Coronary Bypass Grafting," *Ann. Thorac. Surg.* 63(6 Suppl):S64-S67.

Palcic et al. (1991). "Lung Imaging Fluorescence Endoscope: a Device for Detection of Occult Lung Cancer," *Medical Design and Material*, thirteen pages.

Palcic, B. et al. (1990). "Development of a Lung Imaging Fluorescence Endoscope," *Annual International Conference of the IEEE Engineering in Medicine and Biology Society* 12(1):0196-0197.

Palcic, B. et al. (Aug. 1, 1990). "The Importance of Image Quality for Computing Texture Features in Biomedical Specimens," *Proc. SPIE* 1205:155-162.

(56) References Cited

OTHER PUBLICATIONS

Palcic, B. et al. (Jun. 1, 1991). "Lung Imaging Fluorescence Endoscope: Development and Experimental Prototype," *Proc. SPIE* 1448:113-117.

Palcic, B. et al. (Mar. 1991). "Detection and Localization of Early Lung Cancer by Imaging Techniques," *Chest* 99(3):742-743.

Pandharlpande, P.V. et al. (Mar. 2005). "Perfusion Imaging of the Liver: Current Challenges and Future Goals," *Radiology* 234(3):661-673.

Paques, M. et al. (Mar. 2003). "Axon-Tracing Properties of Indocyanine Green," *Arch Ophthalmol.* 121(3):367-370.

Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.

Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.

Peak, M.J. et al. (1986). "DNA-to-Protein Crosslinks and Backbone Breaks Caused by Far- and Near-Ultraviolet and Visible Light Radiations in Mammalian Cells," in *Mechanism of DNA Damage and Repair, Implications for Carcinogenesis and Risk Assessment*, SIMIC, M.G. (ed.) et al., Plenum Press, 233 Spring Street, New York, N.Y. 10013, pp. 193-202.

Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract), three pages.

Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.

Perez, M.T. et al. (Sep. 2002). "In Vivo Studies on Mouse Erythrocytes Linked to Transferrin," *IUBMB Life* 54(3):115-121.

Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).

Phillips, R.P. et al. (1991). "Quantification of Diabetic Maculopathy by Digital Imaging of the Fundus," *Eye* 5(1):130-137.

Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.

Profio, A.E. et al. (Jul.-Aug. 1984). "Fluorometer for Endoscopic Diagnosis of Tumors," *Medical Physics* 11(4):516-520.

Profio, A.E. et al. (Jun. 1, 1991). "Endoscopic Fluorescence Detection of Early Lung Cancer," *Proc. SPIE* 1426:44-46.

Profio, A.E. et al. (Nov./Dec. 1979). "Laser Fluorescence Bronchoscope for Localization of Occult Lung Tumors," *Medical Physics* 6:523-525.

Profio, A.E. et al. (Sep.-Oct. 1986). "Digital Background Subtraction for Fluorescence Imaging," *Medical Physics* 13(5):717-721.

Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.

Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.

Raabe et al. (2009, e-published on Nov. 12, 2008). "Laser Doppler Imaging for Intraoperative Human Brain Mapping", *NeuroImage* 44:1284-1289.

Raabe, A. et al. (Jan. 2003). "Near-Infrared Indocyanine Green Video Angiography: A New Method for Intraoperative Assessment of Vascular Flow," *Neurosurgery* 52(1):132-139.

Rava, R.P. et al. (Jun. 1, 1991). "Early Detection of Dysplasia in Colon and Bladder Tissue Using Laser-Induced Fluorescence," *Proc. SPIE* 1426:68-78.

Razum, N. et al. (Nov. 1987). "Skin Photosensitivity: Duration and Intensity Following Intravenous Hematoporphyrin Derivatives, HpD and DHE, " *Photochemistry and Photobiology* 46(5):925-928.

Report on Observation by C2400-75i and ARGUS20 Under Low illumination conditions, Jan. 17, 2008, six pages.

Request for Invalidation mailed on Jun. 29, 2007 for Japanese Patent No. JP-3881550, filed by Hamamatsu Photonics, Inc., eighty five pages (with English Translation).

Reuthebuch, O et al. (Feb. 2004). "Novadaq SPY: Intraoperative Quality Assessment in Off Pump Coronary Artery Bypass Grafting," *Chest* 125(2):418-424.

Reuthebuch, O.T. et al. (May 2003). "Graft Occlusion After Deployment of the Symmetry Bypass System," *Ann. Thorac. Surg.* 75(5):1626-1629.

Richards-Kortum, R. et al. (Jun. 1991). "Spectroscopic Diagnosis of Colonic Dysplasia: Spectroscopic Analysis," *Biochemistry and Photobiology* 53(6):777-786.

Roberts, W.W. et al. (Dec. 1997). "Laparoscopic Infrared Imaging," *Surg. Endoscopy* 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.

Ropars, C. (ed.) et al. (1987). *Red Blood Cells as Carriers for Drugs. Potential therapeutic Applications*, Pergamon Press, Oxford, New York, pp. v-vii, (Table of Contents only), four pages.

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.

Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.

Rossi, L. et al. (2001). "Erythrocyte-Mediated Delivery of Dexamethasone in Patients with Chronic Obstructive Pulmonary Disease," *Biotechnol. Appl. Biochem.* 33:85-89.

Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.

Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.

Rübben, A. et al. (Mar. 1994). "Infrared Videoangiofluorography of the Skin with Indocyanine Green—Rat Random Cutaneous Flap Model and Results in Man," *Microvascular Research* 47(2):240-251.

Rubens, F.D. et al. (2002). "A New and Simplified Method for Coronary and Graft Imaging During CABG," *The Heart Surgery Forum* 5(2):141-144.

Sakatani, K. et al. (Nov. 1997). "Noninvasive Optical Imaging of the Subarachnoid Space and Cerebrospinal Fluid Pathways Based on Near Infrared Fluorescence," *J. Neurosurg.* 87(5):738-745.

Salmon, E.D. et al. (Oct. 1994). "High Resolution Multimode Digital Imaging System for Mitosis Studies In Vivo and In Vitro," *Biol. Bull* 187(2):231-232.

Sato, M. et al., (1991). "Development of a Visualization Method for the Microcirculation of Deep Viscera Using an Infrared Intravital Microscope System," *Research on ME Devices and ME Technology*, five pages, (with English Translation).

Satpathy G.R. et al. (Oct. 2004; , e-publication Aug. 7, 2004). "Loading Red Blood Cells with Trehalose: A Step Towards Biostabilization," *Cryobiology* 49(2):123-136.

(56) References Cited

OTHER PUBLICATIONS

Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.

Schellingerhout, D. et al. (Oct. 2000). "Quantitation of HSV Mass Distribution in a Rodent Brain Tumor Model," *Gene Therapy* 7(19):1648-1655.

Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.

Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.

Schneider Jr., H.C. et al. (Jan. 1975). "Fluorescence of Testicle, An Indication of Viability of Spermatic Cord After Torsion," *Urology* V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.

Sekijima, M. et al. (Sep. 2004). "An Intraoperative Fluorescent Imaging System in Organ Transplantation," *Transplantation Proceedings* 36(7):2188-2190.

Serov, A. et al. (Mar. 1, 2002). "Laser Doppler Perfusion Imaging with a Complimentary Metal Oxide Semiconductor Image Sensor," *Optics Letters* 27(5):300-302.

Serov, A.N. et al. (Sep. 23, 2003). "Quasi-Parallel Laser Doppler Perfusion Imaging Using a CMOS Image Sensor," *Proc. SPIE* 5067:73-84.

Sezgin, M. et al. (Jan. 2004). "Survey Over Image Thresholding Techniques and Quantitative Performance Evaluation," *Journal of Electronic Imaging* 13(1):146-165.

Sherif, A. et al. (Sep. 2001). "Lymphatic Mapping and Detection of Sentinel Nodes in Patients with Bladder Cancer," *The Journal of Urology* 166(3):812-815.

Sheth, S.A. et al. (Apr. 22, 2004). "Linear and Nonlinear Relationships between Neuronal Activity, Oxygen Metabolism, and Hemodynamic Responses," *Neuron* 42(2):347-355.

Shoaib, T. et al. (Jun. 1, 2001). "The Accuracy of Head and Neck Carcinoma Sentinel Lymph Node Biopsy in the Clinically No Neck," *Cancer* 91(11):2077-2083.

Siemers, B.M. et al. (Nov. 2001). "The Acoustic Advantage of Hunting at Low Heights Above Water: Behaviorual Experiments on the European 'Trawling' Bats Myotis Capaccinii, M Dasycneme and M. Daubentonii," *J. Experimental Biol.* 204(Pt. 22):3843-3854.

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.

Sony Corporation. The Sony U-Matic Videocassette Recorder, VO-9800, ten pages.

Staurenghi, G. et al. (Dec. 2001)."Combining Photodynamic Therapy and Feeder Vessel Photocoagulation: A Pilot Study," *Seminars in Ophthalmology* 16(4):233-236.

Stern, M.D. (Mar. 6, 1975). "In Vivo Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Summary of Invention Submitted to EPO, "Development of Novadaq SPY™ Cardiac Imaging Invention," five pages.

Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.

Takahashi, M. et al. (Sep. 2004). "SPY™: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor, K.M. (Apr. 1998). "Brain Damage During Cardiopulmonary Bypass," *Annals of Thoracic Surgery* 65(4):S20-S26.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.

Torok, B. et al. (May 1996). "Simultaneous Digital Indocyanine Green and Fluorescein Angiography," *Klinische Monatsblatter Fur Augenheilkunde* 208(5):333-336, (Abstract only), two pages.

Tsutsumi, D. et al. "Moisture Detection of road surface using infrared camera," *Reports of the Hokkaido Industrial Research Institute* (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ε-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

(56) References Cited

OTHER PUBLICATIONS

Verbeek, X. et al. (2001). "High-Resolution Functional Imaging With Ultrasound Contrast Agents Based on RF Processing in an In Vivo Kidney Experiment", *Ultrasound in Med. & Biol.* 27(2):223-233.
Wachi, A. et al. (Apr. 1995). "Characteristics of Cerebrospinal Fluid Circulation in Infants as Detected With MR Velocity Imaging," *Child's Nerv Syst* 11(4):227-230.
Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.
Weinbeer, M. et al. (Nov. 25, 2013). "Behavioral Flexibility of the Trawling Long-Legged Bat, Macrophyllum Macrophyllum (Phyllostomidae)," *Frontiers in Physiology* 4(Article 342):1-11.
What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj>, last visited on Jan. 7, 2016, two pages.
Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.
Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.
Wollert, H.G. et al. (Dec. 1989). "Intraoperative Visualization of Coronary Artery Fistula Using Medical Dye," *The Thoracic and Cardiovascular Surg.* 46(6):382-383.
Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.
Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.
Yamaguchi, S. et al. (Apr. 2005). "Evaluation of Skin Perfusion After Nipple-Sparing Mastectomy by Indocyanine Green Dye" *Journal of Saitama Medical University, Japan*, 32(2):45-50, (With English Abstract).
Yoneya, S. et al. (Jun. 1998). "Binding Properties of Indocyanine Green in Human Blood," *IOVS* 39(7):1286-1290.
Yoneya, S. et al. (Sep. 1993). "Improved Visualization of the Choroidal Circulation with Indocyanine Green Angiography," *Arch Opthalmol.* 111(9):1165-1166.
Young. I.T. et al. (1993). "Depth of Focus in Microscopy," SCIA '93, Proc. of the 8th Scandinavian Conference on Image Analysis, Tromso, Norway, pp. 493-498, six pages.
Australian Examination Report No. 1 dated Jun. 26, 2018 for Australian Patent Application No. 2014408488, filed on Mar. 31, 2017, nine pages.
Australian Notice of Allowance dated Sep. 17, 2018 for Australian Patent Application No. 2015327665, filed on Mar. 23, 2017, three pages.
Canadian Notice of Allowance dated Jan. 4, 2018 for Canadian Application No. 2,750,760, filed on Jul. 25, 2008, one page.
Canadian Notice of Allowance dated Sep. 27, 2017 for Canadian Application No. 2,811,847, filed on Mar. 20, 2013, one page.
Canadian Office Action dated Feb. 27, 2017 for Canadian Application No. 2,750,760, filed on Jul. 25, 2011, three pages.
Canadian Office Action dated Feb. 13, 2018 for CA Application No. 2,963,450 filed on Apr. 3, 2017, three pages.
Canadian Office Action dated Feb. 28, 2018 for CA Application No. 2,963,987 filed on Mar. 27, 2017, five pages.
Canadian Office Action dated Jan. 19, 2017 for Canadian Application No. 2,914,778 filed on Dec. 8, 2015, four pages.
Canadian Office Action dated Mar. 16, 2016 for CA Application No. 2,750,760 filed on Jan. 23, 2009, five pages.
Canadian Office Action dated Nov. 28, 2017 for Canadian Application No. 2,914,778 filed on Dec. 8, 2015, six pages.
Canadian Office Action dated Oct. 25, 2016 for Canadian Patent Application No. 2,811,847, filed on Sep. 20, 2011, three pages.
Canadian Office Action dated Sep. 30, 2015 for CA Application No. 2,811,847, filed on Sep. 20, 2011, four pages.
Chinese Fifth Office Action dated Dec. 19, 2017 for Chinese Application No. 201180057244.8 filed on Sep. 20, 2011, eleven pages.
Chinese First Office Action dated Apr. 6, 2017 for Chinese Application No. 201510214021.8, filed on May 14, 2009, fifteen pages.
Chinese Fourth Office Action dated Mar. 13, 2017 for Chinese Application No. 201180057244.8 filed on Sep. 20, 2011, twenty pages.
Chinese Office Action dated Jul. 3, 2012, issued in counterpart Chinese Application No. 200980123414.0, eight pages.
Chinese Office Action dated May 23, 2013, issued in counterpart Chinese Application No. 200980123414.0, nineteen pages.
Chinese Office Action dated Nov. 12, 2015 for Chinese Patent Application No. 201180057244.8, filed on Sep. 20, 2010, five pages, (English Translation).
Chinese Second Office Action dated Feb. 8, 2018 for Chinese Application No. 201510214021.8, filed on May 14, 2009, seventeen pages.
Chinese Third Office Action dated Aug. 8, 2016 for Chinese Application No. 201180057244.8 filed on Sep. 20, 2011, eighteen pages.
Chinese Third Office Action dated Sep. 27, 2018 for Chinese Application No. 201510214021.8, filed on May 14, 2009, seventeen pages.
European Decision in Opposition Proceeding Revoking (Jun. 10, 2010). European Patent No. 1 143 852, thirty pages.
European Decision of European Patent Office Technical Board of Appeal Revoking Counterpart Patent No. 1143852, dated Oct. 23, 2013.
European Decision to Grant dated Apr. 21, 2017 for EP Application No. 09732993.2, filed on Nov. 8, 2010, two pages.
European Decision to Grant dated Mar. 15, 2018 for EP Application No. 09739980.2 filed on Nov. 30, 2010, two pages.
European Extended Search Report dated Apr. 28, 2014 for EP Application No. 09 732 993.2, filed on Apr. 14, 2008, eight pages.
European Extended Search Report dated Feb. 22, 2012 for EP Application No. 09 704 642.9, filed on Jan. 25, 2008, fifteen pages.
European Extended Search Report dated Jan. 28, 2014 for EP Application No. 11 826 475.3, filed on Sep. 20, 2010, six pages.
European Extended Search Report dated Jun. 6, 2018 for EP Application No. 18166591.0 filed on Apr. 10, 2018, six pages.
European Extended Search Report dated May 23, 2018 for EP Application No. 14903635.2 filed on May 2, 2017, nine pages.
European Extended Search Report dated Oct. 14, 2015 for EP Application No. 13806313.6 filed on Jun. 20, 2013, nine pages.
European Extended Search Report dated Sep. 16, 2016 for EP Application No. 16183434.6 filed on Aug. 9, 2016, ten pages.
European Notice of Allowance dated Oct. 21, 2015 for EP Application No. 11 826 475.3, filed on Sep. 20, 2010, eight pages.
European Notice of Allowance dated Oct. 29, 2015 for EP Application No. 09 704 642.9, filed on Jan. 25, 2008, two pages.
European Office Action—Communication in pursuant to Article 94(3) EPC dated Mar. 9, 2016 for European Patent Application No. 09739980.2 filed May 1, 2009, five pages.
European Office Action—Communication Pursuant to Article 94(3) EPC dated Apr. 6, 2018 for EP Application No. 15188378.2 filed on Oct. 5, 2015, four pages.
European Office Action—Communication Pursuant to Article 94(3) EPC dated Aug. 31, 2017 for EP Application No. 09739980.2 filed on Nov. 30, 2010, four pages.
European Office Action—Communication pursuant to Article 94(3) dated May 27, 2016 for EP Application No. 15160177.0 filed on Aug. 11, 2000, five pages.
European Office Action—Communication Pursuant to Article 94(3) dated Sep. 21, 2017 for European Application No. 16163909.1 filed on Apr. 5, 2016, three pages.
European Office Action—Communication pursuant to Rules 70(2) and 70a(2) EPC dated May 15, 2014 in EP Application No. 09732993.2, one page.

(56) References Cited

OTHER PUBLICATIONS

European Office Action—Communication pursuant to Rules 70(2) and 70a(2) EPC dated Nov. 14, 2016 in EP Application No. 16163909.1, two pages.
European Office Action—Communication Under Rule 71(3) EPC (Intention to Grant) dated Dec. 1, 2017 for European patent Application No. 09739980.2, filed on Nov. 30, 2010, seven pages.
European Office Action—Communication under Rule 71(3) EPC (Intention to Grant) dated Nov. 21, 2017 for European Patent Application No. 15160177.0, filed on Aug. 11, 2000, seven pages.
European Office Action dated Mar. 27, 2015 for EP Application No. 09 732 993.2, filed on Apr. 14, 2008, six pages.
European Office Action dated May 28, 2018 for EP Application No. 16183434.6 filed on Aug. 9, 2016, four pages.
European Opposition of European Patent No. EP1143852 lodged by Hamamatsu Photonics, Inc., Jul. 30, 2008.
European Partial Search Report dated Dec. 16, 2010 for European Application No. 10186218.3 filed on Aug. 11, 2000, seven pages.
European Partial Search Report dated Jan. 10, 2018 for EP Application No. 17171383.7 filed on May 16, 2017, eleven pages.
European Partial Search Report dated Jun. 11, 2014 for European Application No. 13178642.8, filed on May 1, 2009, five pages.
European Partial Search Report dated Jun. 28, 2016 for European Application No. 16163909.1 filed on Apr. 5, 2016, six pages.
European Summons to attend Oral Proceedings pursuant to Rule 115(1) EPC dated Apr. 25, 2016 for European patent application No. 09732993.2, filed on Apr. 14, 2009, 5 pages.
European Summons to attend Oral Proceedings pursuant to Rule 115(1) EPC dated Dec. 16, 2016 for European patent application No. 15160177.0, filed on Aug. 11, 2000, seven pages.
European Supplemental Search Report dated Jul. 6, 2004 for EP Application No. 00955472.6 filed on Aug. 11, 2000, five pages.
Indian Examination Report dated Jan. 16, 2018 for Indian Application No. 2993/DELNP/2011, filed on Apr. 25, 2011, eleven pages.
Indian Examination Report dated Jul. 28, 2017 for Indian Application No. 1983/MUMNP/2007, filed on Nov. 27, 2007, seven pages.
Indian Examination Report dated Sep. 22, 2016 for Indian Application No. 7566/DELNP/2010, filed on Oct. 27, 2010, nine pages.
International Preliminary Examination Report completed on Jul. 1, 2001 for PCT/US00/22088, filed on Aug. 11, 2000, three pages.
International Preliminary Report on Patentability dated Apr. 4, 2017 for PCT Application No. PCT/CA2015/050973 filed on Sep. 28, 2015, six pages.
International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report and Written Opinion dated Oct. 24, 2017 for PCT Application No. PCT/CA2017/050564 filed on May 10, 2017, fourteen pages.
International Search Report dated Dec. 3, 2015 for PCT Application No. PCT/CA2015/050973 filed on Sep. 28, 2015, three pages.
International Search Report dated Jul. 4, 2008 for PCT Patent Application No. PCT/US2007/080847, filed on Oct. 9, 2007, three pages.
International Search Report dated Dec. 3, 2009 for PCT Patent Application No. PCT/IB2009/005700, filed on Apr. 14, 2009, three pages.
International Search Report dated Feb. 1, 2012 for PCT Patent Application No. PCT/IB2011/002381, filed on Sep. 20, 2011, five pages.
International Search Report dated Jan. 22, 2014 for PCT Application No. PCT/IB2013/001934, filed on Jun. 20, 2013, four pages.
International Search Report dated Jun. 2, 2009 for PCT Application No. PCT/EP2008/008547, filed on Oct. 9, 2008, five pages.
International Search Report dated Jun. 8, 2009 for PCT Patent Application No. PCT/CA2009/000073, filed on Jan. 23, 2009, three pages.
International Search Report dated Oct. 18, 2000 for PCT Application No. PCT/US2000/22088, filed on Aug. 11, 2000, one page.
International Search Report dated Sep. 11, 2009 for Application No. PCT/US2009/042606 filed on May 1, 2009, five pages.
Invitation to Pay Additional Fees and, Where Applicable, Protest Fee dated Jul. 4, 2017 for PCT/CA2017/050564, filed on May 10, 2017, two pages.
Japanese Final Office Action dated Feb. 5, 2018 for Japanese Patent Application No. 2016-014503, filed on Jan. 28, 2016, six pages.
Japanese Final Office Action dated Sep. 25, 2018 for Japanese Application No. 2017-518785 filed on Apr. 7, 2017, six pages.
Japanese First Office Action dated Feb. 1, 2016 for Japanese Patent Application No. 2015-517876 filed Jun. 20, 2013, eight pages.
Japanese First Office Action dated Jul. 28, 2017 for Japanese Patent Application No. 2016-203798 filed Oct. 17, 2016, four pages.
Japanese Notice of Allowance dated Jun. 8, 2018 for Japanese Patent Application No. 2016-203798 filed Oct. 17, 2016, six pages.
Japanese Notice of Allowance dated Sep. 16, 2016 for Japanese Patient Application No. 2015-517876 filed on Jun. 20, 2013, six pages.
Japanese Notice of Allowance dated Sep. 25, 2017 for Japanese Patent Application No. 2013-529729, filed on Mar. 21, 2013, six pages.
Japanese Office Action dated Apr. 1, 2016 for Japanese Patent Application No. 2013-529729, filed on Mar. 21, 2013, seven pages.
Japanese Office Action dated Aug. 20, 2018 for Japanese Patent Application No. 2017-205499, filed on Nov. 24, 2017, six pages.
Japanese Office Action dated Jul. 30, 2013, issued in counterpart Japanese Application No. 2011-504574, filed Apr. 14, 2009, six pages.
Japanese Office Action dated Mar. 3, 2017 for Japanese Patent Application No. 2016-014503, filed on Jan. 28, 2016, ten pages.
Japanese Office Action dated Mar. 19, 2018 for Japanese Application No. 2017-518785 filed on Apr. 7, 2017, eight pages.
Japanese Office Action dated Mar. 31, 2017 for Japanese Patent Application No. 2013-529729, filed on Mar. 21, 2013, eleven pages.
Japanese Office Action dated May 7, 2018 for Japanese Patent Application No. 2017-516925 filed on Mar. 28, 2017, four pages.
Japanese Office Action dated Sep. 14, 2015 for Japanese Patent Application No. 2011-504574, filed on Apr. 14, 2009, three pages.
Korean Notice of Allowance dated Apr. 27, 2017 for Korean Patent Application No. 10-2016-7007994, filed on Mar. 25, 2016, three pages.
Korean Notice of Allowance dated Apr. 29, 2016 for Korean Patent Application No. 10-2010-7024977, filed on Apr. 14, 2009, three pages.
Korean Office Action dated Apr. 17, 2018 for Korean Patent Application No. 10-2017-7012463, filed on May 8, 2017, six pages.
Korean Office Action dated Nov. 30, 2015 for Korean Patent Application No. 10-2010-7024977, filed on Apr. 14, 2009, two pages.
Korean Patent Office Action dated Jun. 25, 2014 in Korean Patent Application No. 10-2013-7035027, filed on May 14, 2009, fifteen pages.
Mexican Office Action dated May 30, 2013, issued in counterpart Mexican Application No. MX/a/2010/011249.
Novadaq Technologies Inc.'s Preliminary Response filed on Aug. 23, 2017 to Petition for Inter Partes Review of U.S. Pat. No. 8,892,190 sixty one pages.
Petition for Inter Partes Review of U.S. Pat. No. 8,892,190 (May 11, 2017), filed by Visionsense Corp., fifty four pages.
Russian Decision on Grant dated Jul. 29, 2013, issued in counterpart Russian Application No. 2011111078.14, five pages.
Russian Office Action dated Mar. 29, 2013, issued in counterpart Russian Application No. 2011111078.14, three pages.
Translation of Decision of Japanese Patent Office Trial Board revoking Counterpart Patent No. U.S. Pat. No. 3,881,550, twenty six pages.
U.S. Final Office Action dated Apr. 2, 2013 for U.S. Appl. No. 13/419,368, filed Mar. 13, 2012, five pages.
U.S. Final Office Action dated Apr. 4, 2017 for U.S. Appl. No. 12/933,477, filed Sep. 20, 2010, twelve pages.

(56) References Cited

OTHER PUBLICATIONS

U.S. Final Office Action dated Apr. 10, 2008 for U.S. Appl. No. 11/106,154, filed Apr. 14, 2005, six pages.
U.S. Final Office Action dated Apr. 12, 2017 for U.S. Appl. No. 14/543,429, filed Nov. 17, 2014, nine pages.
U.S. Final Office Action dated Apr. 20, 2016 for U.S. Appl. No. 14/543,429, filed Nov. 17, 2014, seven pages.
U.S. Final Office Action dated Apr. 27, 2011 for U.S. Appl. No. 11/515,419, filed Sep. 1, 2006, nine pages.
U.S. Final Office Action dated Aug. 10, 2012 for U.S. Appl. No. 11/912,877, filed Aug. 13, 2008, ten pages.
U.S. Final Office Action dated Dec. 31, 2015 for U.S. Appl. No. 14/177,050 filed Feb. 10, 2014, eighteen pages.
U.S. Final Office Action dated Feb. 4, 2015 for U.S. Appl. No. 13/314,418, filed Dec. 8, 2011, six pages.
U.S. Final Office Action dated Feb. 13, 2015 for U.S. Appl. No. 14/543,429, filed Nov. 17, 2014, six pages.
U.S. Final Office Action dated Feb. 18, 2010 for U.S. Appl. No. 11/106,154, filed Apr. 14, 2005, six pages.
U.S. Final Office Action dated Jul. 9, 2015 for U.S. Appl. No. 14/543,356, filed Nov. 17, 2014, eight pages.
U.S. Final Office Action dated Jul. 21, 2016 for U.S. Appl. No. 14/543,356, filed Nov. 17, 2014, seven pages.
U.S. Final Office Action dated Jun. 1, 2015 for U.S. Appl. No. 14/543,429, filed Nov. 17, 2014, nine pages.
U.S. Final Office Action dated Jun. 25, 2014 for U.S. Appl. No. 12/933,477, filed Sep. 20, 2010, fifteen pages.
U.S. Final Office Action dated Mar. 20, 2017 for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013 for U.S. Appl. No. 12/933,477, filed Sep. 20, 2010, twelve pages.
U.S. Final Office Action dated Nov. 6, 2013 for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011 for U.S. Appl. No. 11/106,154, filed Apr. 14, 2005, five pages.
U.S. Final Office Action dated Sep. 17, 2014 for U.S. Appl. No. 11/515,419, filed Sep. 1, 2006, eleven pages.
U.S. Final Office Action dated Sep. 17, 2015 for U.S. Appl. No. 12/933,477, filed Sep. 20, 2010, six pages.
U.S. Final Office Action dated Sep. 23, 2004 for U.S. Appl. No. 09/744,034, filed Apr. 27, 2001, seven pages.
U.S. Final Office Action dated Sep. 29, 2016 for U.S. Appl. No. 13/922,996, filed Jun. 20, 2013, fourteen pages.
U.S. Non-Final Office Action dated Apr. 1, 2015 for U.S. Appl. No. 12/933,477, filed Sep. 20, 2010, fourteen pages.
U.S. Non-Final Office Action dated Apr. 28, 2010 for U.S. Appl. No. 11/946,672, filed Nov. 28, 2007, nine pages.
U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 16, 2016 for U.S. Appl. No. 14/868,369, filed Sep. 28, 2015, seven pages.
U.S. Non-Final Office Action dated Dec. 20, 2013 for U.S. Appl. No. 12/933,477, filed Sep. 20, 2010, thirteen pages.
U.S. Non-Final Office Action dated Dec. 30, 2010 for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016 for U.S. Appl. No. 14/543,356, filed Nov. 17, 2014, seven pages.
U.S. Non-Final Office Action dated Jan. 8, 2018 for U.S. Appl. No. 15/077,677, filed Mar. 22, 2016, nine pages.
U.S. Non-Final Office Action dated Jan. 9, 2009 for U.S. Appl. No. 11/106,154, filed Apr. 14, 2005, six pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012 for U.S. Appl. No. 11/912,877, filed Aug. 13, 2008, eleven pages.
U.S. Non-Final Office Action dated Jan. 31, 2018 for U.S. Appl. No. 15/799,727 filed Oct. 31, 2017, seven pages.
U.S. Non-Final Office Action dated Jul. 2, 2015 for U.S. Appl. No. 14/177,050, filed Feb. 10, 2014, nineteen pages.
U.S. Non-Final Office Action dated Jul. 8, 2014 for U.S. Appl. No. 13/314,418, filed Dec. 8, 2011, seven pages.
U.S. Non-Final Office Action dated Jul. 22, 2015 for U.S. Appl. No. 13/314,418, filed Dec. 8, 2011, six pages.
U.S. Non-Final Office Action dated Jun. 11, 2013 for U.S. Appl. No. 11/515,419, filed Sep. 1, 2006, eleven pages.
U.S. Non-Final Office Action dated Jun. 28, 2012 for U.S. Appl. No. 12/063,349, filed May 12, 2010, seventeen pages.
U.S. Non-Final Office Action dated Mar. 6, 2007 for U.S. Appl. No. 11/106,154, filed Apr. 14, 2005, eight pages.
U.S. Non-Final Office Action dated Mar. 10, 2004 for U.S. Appl. No. 09/744,034, filed Apr. 27, 2001, seven pages.
U.S. Non-Final Office Action dated Mar. 13, 2015 for U.S. Appl. No. 14/543,356, filed Nov. 17, 2014, eight pages.
U.S. Non-Final Office Action dated Mar. 22, 2018 for U.S. Appl. No. 15/610,102, filed May 31, 2017, eleven pages.
U.S. Non-Final Office Action dated May 6, 2015 for U.S. Appl. No. 12/063,349, filed May 12, 2010, seventeen pages.
U.S. Non-Final Office Action dated May 21, 2015 for U.S. Appl. No. 13/922,996, filed Jun. 20, 2013, fourteen pages.
U.S. Non-Final Office Action dated Nov. 9, 2015 for U.S. Appl. No. 14/177,045, filed Feb. 10, 2014, seven pages.
U.S. Non-Final Office Action dated Nov. 18, 2016 for U.S. Appl. No. 12/933,477, filed Sep. 20, 2010, six pages.
U.S. Non-Final Office Action dated Nov. 27, 2015 for U.S. Appl. No. 14/543,429, filed Nov. 17, 2014, six pages.
U.S. Non-Final Office Action dated Oct. 12, 2016 for U.S. Appl. No. 14/543,429, filed Nov. 17, 2014, nine pages.
U.S. Non-Final Office Action dated Oct. 13, 2017 for U.S. Appl. No. 13/922,996, filed Jun. 20, 2013, seventeen pages.
U.S. Non-Final Office Action dated Oct. 26, 2017 for U.S. Appl. No. 14/543,429, filed Nov. 17, 2014, nine pages.
U.S. Non-Final Office Action dated Oct. 28, 2016 for U.S. Appl. No. 14/543,356, filed Nov. 17, 2014, eight pages.
U.S. Non-Final Office Action dated Sep. 5, 2012 for U.S. Appl. No. 12/933,477, filed Sep. 20, 2010, seven pages.
U.S. Non-Final Office Action dated Sep. 15, 2010 for U.S. Appl. No. 11/106,154, filed Apr. 14, 2005, six pages.
U.S. Non-Final Office Action dated Sep. 27, 2017 for U.S. Appl. No. 14/177,050, filed Feb. 10, 2014, twenty two pages.
U.S. Non-Final Office Action dated Sep. 30, 2010 for U.S. Appl. No. 11/515,419, filed Sep. 1, 2006, eleven pages.
U.S. Notice of Allowance dated Apr. 17, 2014 for U.S. Appl. No. 13/419,368, filed Mar. 13, 2012, five pages.
U.S. Notice of Allowance dated Aug. 7, 2014 for U.S. Appl. No. 13/850,063, filed Mar. 25, 2013, nine pages.
U.S. Notice of Allowance dated Dec. 2, 2016 for U.S. Appl. No. 14/598,832, filed Jan. 16, 2015, seven pages.
U.S. Notice of Allowance dated Dec. 6, 2017 for U.S. Appl. No. 15/476,290, filed Mar. 31, 2017, nine pages.
U.S. Notice of Allowance dated Jul. 12, 2017 for U.S. Appl. No. 14/868,369, filed Sep. 28, 2015, nine pages.
U.S. Notice of Allowance dated Jul. 13, 2016 for U.S. Appl. No. 14/598,832, filed Jan. 16, 2015, seven pages.
U.S. Notice of Allowance dated Jun. 15, 2018 for U.S. Appl. No. 11/515,419, filed Sep. 1, 2006, five pages.
U.S. Notice of Allowance dated Mar. 7, 2005 for U.S. Appl. No. 09/744,034, filed Apr. 27, 2001, five pages.
U.S. Notice of Allowance dated Mar. 15, 2016 for U.S. Appl. No. 14/598,832, filed Jan. 16, 2015, seven pages.
U.S. Notice of Allowance dated Mar. 29, 2018 for U.S. Appl. No. 14/177,050, filed Feb. 10, 2014, ten pages.
U.S. Notice of Allowance dated May 26, 2016 for U.S. Appl. No. 14/177,045, filed Feb. 10, 2014, eight pages.

(56) References Cited

OTHER PUBLICATIONS

U.S. Notice of Allowance dated Nov. 25, 2015 for U.S. Appl. No. 14/598,832, filed Jan. 16, 2015, seven pages.
U.S. Notice of Allowance dated Nov. 30, 2010 for U.S. Appl. No. 11/946,672, filed Nov. 28, 2007, six pages.
U.S. Notice of Allowance dated Oct. 4, 2013 for U.S. Appl. No. 11/912,877, filed Aug. 13, 2008, nine pages.
U.S. Notice of Allowance dated Oct. 6, 2014 for U.S. Appl. No. 13/419,368, filed Mar. 13, 2012, five pages.
U.S. Notice of Allowance dated Oct. 16, 2014 for U.S. Appl. No. 13/850,063, filed Mar. 25, 2013, eight pages.
U.S. Notice of Allowance dated Oct. 17, 2018 for U.S. Appl. No. 12/933,477, filed Sep. 20, 2010, seven pages.
U.S. Notice of Allowance dated Oct. 18, 2012 for U.S. Appl. No. 12/841,659, filed Jul. 22, 2010, seven pages.
U.S. Notice of Allowance dated Sep. 6, 2018 for U.S. Appl. No. 13/922,996, filed Jun. 20, 2013, nine pages.
U.S. Notice of Allowance dated Sep. 26, 2018 for U.S. Appl. No. 15/610,102, filed May 31, 2017, eight pages.
U.S. Notice of Allowance dated Sep. 11, 2018 for U.S. Appl. No. 15/799,727, filed Oct. 31, 2017, eight pages.
U.S. Restriction Requirement dated Jun. 26, 2017 for U.S. Appl. No. 15/077,677, filed Mar. 22, 2016, seven pages.
Written Opinion of the International Searching Authority dated Jul. 4, 2008 for PCT Patent Application No. PCT/US2007/080847, filed on Oct. 9, 2007, six pages.
Written Opinion of the International Searching Authority dated Dec. 3, 2009 for PCT Patent Application No. PCT/IB2009/005700, filed on Apr. 14, 2009, six pages.
Written Opinion of the International Searching Authority dated Dec. 3, 2015 for PCT Patent Application No. PCT/CA2015/050973 filed on Sep. 28, 2015, five pages.
Written Opinion of the International Searching Authority dated Feb. 1, 2012 for PCT Patent Application No. PCT/IB2011/002381, filed on Sep. 20, 2011, four pages.
Written Opinion of the International Searching Authority dated Jan. 22, 2014 for PCT Patent Application No. PCT/IB2013/001934, filed on Jun. 20, 2013, six pages.
Written Opinion of the International Searching Authority dated Jun. 2, 2009 for PCT Patent Application No. PCT/EP2008/008547, filed on Oct. 9, 2008, eleven pages.
Written Opinion of the International Searching Authority dated Jun. 8, 2009 for PCT Patent Application No. PCT/CA2009/000073, filed on Jan. 23, 2009, four pages.
U.S. Appl. No. 16/030,126, filed Jul. 9, 2018.

\* cited by examiner

NEAR INFRA RED FLUORESCENCE IMAGING FOR VISUALIZATION OF BLOOD VESSELS DURING ENDOSCOPIC HARVEST

CROSS-REFERENCE TO RELATED APPLICATIONS

This application claims priority to U.S. Provisional Application Ser. No. 61/176,642, filed May 8, 2009, the entire content is incorporated herein by reference.

BACKGROUND OF THE INVENTION

Endoscopic Vein Harvest (EVH) has become the standard method for dissection and harvest of conduit used in coronary artery bypass surgery (CABG). Recent data show that, while overwhelmingly preferred by patients, EVH has been associated with a decrease in long-term graft patency rates. While yet to be definitively ascertained, this adverse outcome is thought to be associated with vessel trauma incurred during the endoscopic harvest procedure.

Currently, identification of blood vessels to be harvested endoscopically relies upon locating the vessel by white-light visual guidance. Following the course of the vessel during dissection and recognizing of side branches of this vessel by white light imaging is often problematic. Difficulties in recognizing the course of the vessel and/or identifying side branches may lead to trauma to the vessel, with the potential for sub optimal patient outcome.

Accordingly, there is a need to identify an appropriate vessel, to track the course of the vessel and to identify side branches; for example, this can be accomplished by observing a fluorescence image of the vessel of interest and allowing this image to be displayed in a manner that permits full appreciation of the anatomy.

The search for a more favorable imaging modality is continuing, with recent interest in the use of indocyanine green (ICG) fluorescence imaging, wherein blood circulation is assessed on the basis of a fluorescence signal. Fluorescence in ICG with an emission peak around 830 nm occurs as a result of excitation by radiation in the near-infrared spectral range. Excitation light with a wavelength around 800 nm can be produced, for example, by a diode laser, light emitting diode (LED), or other conventional illumination sources, such as arc lamps, halogen lamps in conjunction with a suitable bandpass filter.

ICG strongly binds to blood proteins and has previously been used for cardiac output measurement, hepatic function evaluation, and ophthalmic angiography, with few adverse reactions. ICG fluorescence imaging previously has been successfully used to assess and validate patency of arterial and venous anastomoses to identify insufficient ones that might lead to post-operative flap and graft failure.

However, there is still need to improve preoperative location and, optionally, the determination of the dimensions of blood vessels to be harvested in an endoscopic procedure by a simple, minimally-invasive method. This invention addresses these needs.

SUMMARY OF THE INVENTION

According to one aspect of the invention, a method for endoscopic preoperative identification of a harvestable vessel during surgery is disclosed, which includes the steps of locating a candidate vessel, injecting a quantity of ICG into the patient, illuminating the vessel with suitable excitation light and observing ICG fluorescence through the optics of an endoscope.

In one embodiment, after the location of the vessel has been marked, the vessel(s) may be dissected, harvested and transplanted to the diseased or traumatized area to be reconstructed or reperfused. The vessel may preferably be harvested from the lower leg of a patient.

In another embodiment, the vessel tortuousity and the presence of side-branches is evaluated to reduce/prevent the potential of vessel trauma and subsequent related adverse outcomes.

In one embodiment, the quantity of ICG may be injected as a bolus or as a quantity of autologous blood when there is a significant amount of stasis in the blood vessel of interest.

In yet another embodiment, if the vessel collapses during harvest, the endoscope provides the means by which to insufflate the vessel with a bolus of blood (preferably autologous) containing ICG at a concentration that produces optimal fluorescence.

These and other features and advantages of the present invention will become more readily appreciated from the detailed description of the invention that follows.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIG. 2 is a white-light and fluorescence image of an identified vessel according to the invention.

DETAILED DESCRIPTION

Figure 1:
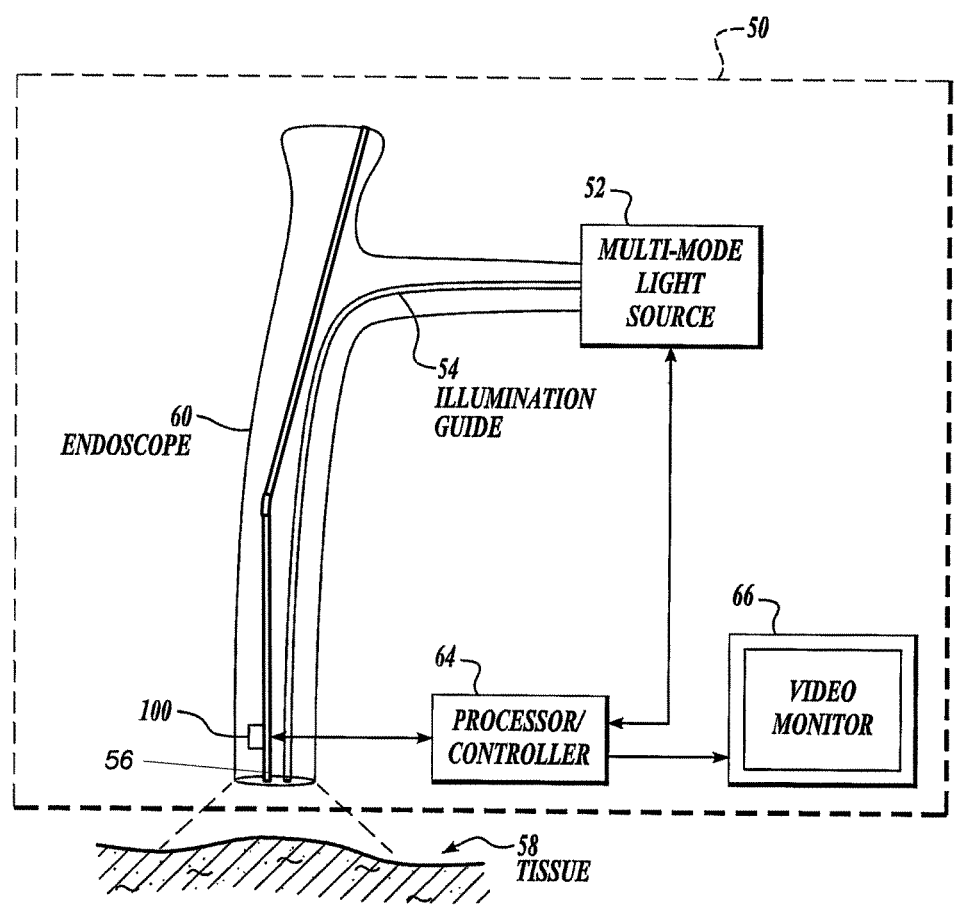
FIG. 1 shows schematically an endoscopic system for observing ICG fluorescence.

The invention is directed to preoperative/intra-operative determination of the location of vessels to be harvested endoscopically and to enhance visualization of them of them throughout the procedure.

The system includes a multi-mode light source 52 that generates light for obtaining color and fluorescence images. The use of the light source for obtaining different kinds of images will be described in further detail below. Light from the light source 52 is supplied to an illumination guide 54 of an endoscope 60, which then illuminates a tissue sample 58 that is to be imaged. The system also includes a camera 100 located at the insertion end of the endoscope 60. The light from the tissue is directly captured by the camera 100. The endoscope 60 is similar to conventional video endoscopes, but with the added capability to provide both fluorescence/reflectance and/or fluorescence/fluorescence imaging in additional to conventional color imaging. For vessel insufflation, it also incorporates a needle-tipped catheter 56 configured for insertion through the port of the endoscope 60 for infusion of intravascular introduction of fluids.

A processor/controller 64 controls the camera 100 and the light source 52, and produces video signals that are displayed on a video monitor 66. The processor/controller 64 communicates with the camera 100 with wires or other signal carrying devices that are routed within the endoscope. Alternatively, communication between the processor/controller 64 and the camera 100 can be conducted over a wireless link.

The multimode light source 52 may include a laser light source that illuminates an area of interest. However, other light sources, such as LEDs, or other conventional illumination sources, such as arc lamps, halogen lamps in conjunction with a suitable bandpass filter, may be used. The area of interest may vary based on surgical requirements and the available illumination intensity and camera sensitivity.

A filter (not shown) is typically placed in front of the camera lens to block excitation light from reaching the camera sensor, while allowing fluorescence light to pass through. The filter may be an NIR long-wave pass filter (cut filter), which is only transparent to wavelengths greater than about 815 nm, or preferably a bandpass filter transmitting at peak wavelengths of between 830 and 845 nm and having a full width at half maximum (FWHM) transmission window of between about 10 nm and 25 nm, i.e. outside the excitation wavelength band. The camera 100 may also be designed to acquire a color image of the area of interest to allow real-time correlation between the fluorescence image and the color image.

In the context of the present invention, the device illustrated in FIG. 1 can be used to:

1. Identify/locate in situ vessels—this will assist the operator in selecting vessels required for use during the subsequent procedure.
2. Facilitate visualization of a target vessel during harvest when iatrogenic isolation of the vessel from its systemic blood supply causes the vessel to collapse by providing a means for insufflation.
3. Validate anastomotic patency and arterial and venous flow—this can potentially improve outcomes to eliminate transplant failure which can be a result of poor arterial flow and inadequate perfusion as well as poor venous return resulting in congestion.
4. Visualize and confirm complete tissue perfusion.

As an important aspect of the invention, suitable vessels are identified with high accuracy so as to reduce unnecessary trauma.

Currently identification of blood vessels to be harvested endoscopically relies upon locating the vessel by palpation and visual inspection. Following the course of the vessel during dissection and recognition of side branches of this vessel is performed by white light imaging and is often problematic. Difficulties in recognizing the course of the vessel or identifying side branches may lead to trauma to the vessel with the potential for sub optimal patient outcome. Moreover, situations often arise during harvest when determining the course of the vessel becomes very difficult; an example of this is harvest of the saphenous vein, which usually is easily tracked and excised from the ankle to the knee, but distally becomes very difficult to track, especially if it collapses. The present invention greatly facilities identification of the vessel, ability to track the course of the vessel and early recognition of side branches by providing selective contrast (fluorescence) to the vessel of interest and allowing this selective contrast to be displayed in a manner that permits full appreciation of the anatomy.

FIG. 2 shows a white-light image (upper left corner of the Figure) and fluorescence image (lower left corner of the Figure) of an identified vessel according to the invention, as well as an overlay of the fluorescence and white-light image (right part of the Figure).

For the application of fluorescence endoscopy video system to endoscopic vessel harvest, the system was tested on a human population (with IRB approval) on March 23, 24 and 26, 2009 at East Carolina University (Greenville, N.C.). The first study was a dose-finding study in one patient and based on the data from this patient a second patient was imaged using a higher dose. In the course of this second study excellent image quality was achieved and, in fact, the system demonstrated its utility by locating a vessel that was not detectable by other currently available methods. Subsequent studies confirmed the consistency of image quality and ability to detect side branches during endoscopic harvest of the greater saphenous vein.

Using endoscopic ICG fluorescence imaging endoscopic vessel harvest may enhance or improve surgical outcomes due to the ability to readily identify the vessel, track the course of the vessel and quickly detect the presence of side branches via selective contrast during endoscopic harvest.

The described embodiments detect a fluorescence signal emitted transcutaneously by ICG following excitation in the near-infrared spectral range. However, those skilled in the art will appreciate that other dyes which can be excited and emit fluorescence in a spectral range where tissue transmits light can also be used. It is envisioned to use a version of the fluorescence endoscopy video system also as an aid in endoscopic vessel harvest during coronary artery bypass procedures.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the appended claims.

What is claimed is:

1. A method for enhancing endoscopic identification and dissection of a blood vessel in tissue during endoscopic harvest, comprising the steps of:
   introducing an endoscope to a target region containing a blood vessel to be harvested;
   injecting ICG into the bloodstream;
   illuminating the blood vessel in situ, via a multi-mode light source, with excitation light capable of exciting fluorescence in the ICG;
   capturing, via a camera, fluorescence and color images of the blood vessel in situ;
   providing, via a processor, video signals to a display to facilitate visualization of the blood vessel in situ;
   locating the blood vessel to be harvested by observing the ICG fluorescence; and
   harvesting the located blood vessel for use in a subsequent procedure.

2. The method of claim 1, further comprising the step of: identifying vessel branches from ICG fluorescence intensity in the vessel branches and absence of ICG fluorescence in tissue surrounding the vessel branches.

3. The method of claim 1, further comprising the step of harvesting the blood vessel by:
   before said harvesting, incising an area where the blood vessel to be harvested is located, said harvesting including harvesting at least the located blood vessel; and
   transplanting at least the harvested blood vessel to a diseased or traumatized area to be reconstructed.

4. The method of claim 1, further comprising the step of tracking a course of the blood vessel during dissection by observing the ICG fluorescence.

5. The method of claim 1, wherein the ICG is injected as a bolus.

6. The method of claim 1, wherein the ICG is injected as autologous blood for identifying the blood vessel in the presence of stasis in the blood vessel.

7. A method for identifying and dissecting a collapsed blood vessel during endoscopic harvest, comprising the steps of:
inserting a needle-tipped catheter introduced through a port of an endoscope into the collapsed blood vessel;
injecting, via the catheter, into the collapsed blood vessel a bolus containing ICG to re-inflate the blood vessel;
illuminating the blood vessel in situ, via a multi-mode light source, with excitation light capable of exciting fluorescence in the ICG;
capturing, via a camera, fluorescence and color images of the blood vessel in situ;
providing, via a processor, video signals to a display to facilitate visualization of the blood vessel in situ; and
locating the re-inflated blood vessel to be harvested by observing the ICG fluorescence.

8. The method of claim 5, wherein the bolus comprises autologous blood containing ICG at a concentration in the range of 0.01 to 0.05 mg per ml of blood.

9. The method of claim 7, further comprising imaging, via a camera associated with the endoscope, the re-inflated blood vessel to be harvested.

10. The method of claim 7, further comprising harvesting the located re-inflated blood vessel.

11. The method of claim 1, further comprising imaging, via a camera associated with the endoscope, the blood vessel to be harvested.

12. The method of claim 1, further comprising carrying out a subsequent procedure using said harvested blood vessel.

13. A method for enhancing endoscopic identification and dissection of a blood vessel in tissue during endoscopic harvest, comprising the steps of:
introducing an endoscope to a target region containing a blood vessel to be harvested;
injecting ICG into the bloodstream;
illuminating the blood vessel in situ, via a multi-mode light source, with excitation light capable of exciting fluorescence in the ICG;
capturing, via a camera, fluorescence and color images of the blood vessel in situ;
providing, via a processor, video signals to a display to facilitate visualization of the blood vessel in situ; and
harvesting the visualized blood vessel for use in a subsequent procedure.

14. The method of claim 13, further comprising:
identifying vessel branches from ICG fluorescence intensity in the vessel branches and absence of ICG fluorescence in tissue surrounding the vessel branches.

15. The method of claim 13, further comprising the step of harvesting the blood vessel by:
before said harvesting, incising an area where the blood vessel to be harvested is located, said harvesting including harvesting at least the located blood vessel; and
transplanting at least the harvested blood vessel to a diseased or traumatized area to be reconstructed.

16. The method of claim 13, further comprising the step of tracking a course of the blood vessel during dissection by observing the ICG fluorescence.

17. The method of claim 13, wherein the ICG is injected as a bolus.

18. The method of claim 13, wherein the ICG is injected as autologous blood for identifying the blood vessel in the presence of stasis in the blood vessel.

19. The method of claim 13, further comprising carrying out a subsequent procedure using said harvested blood vessel.

20. The method of claim 7, further comprising carrying out a subsequent procedure using said harvested blood vessel.

* * * * *